May 16, 1933. L. BURBANK Plant Pat. 66
ROSE
Filed July 18, 1932
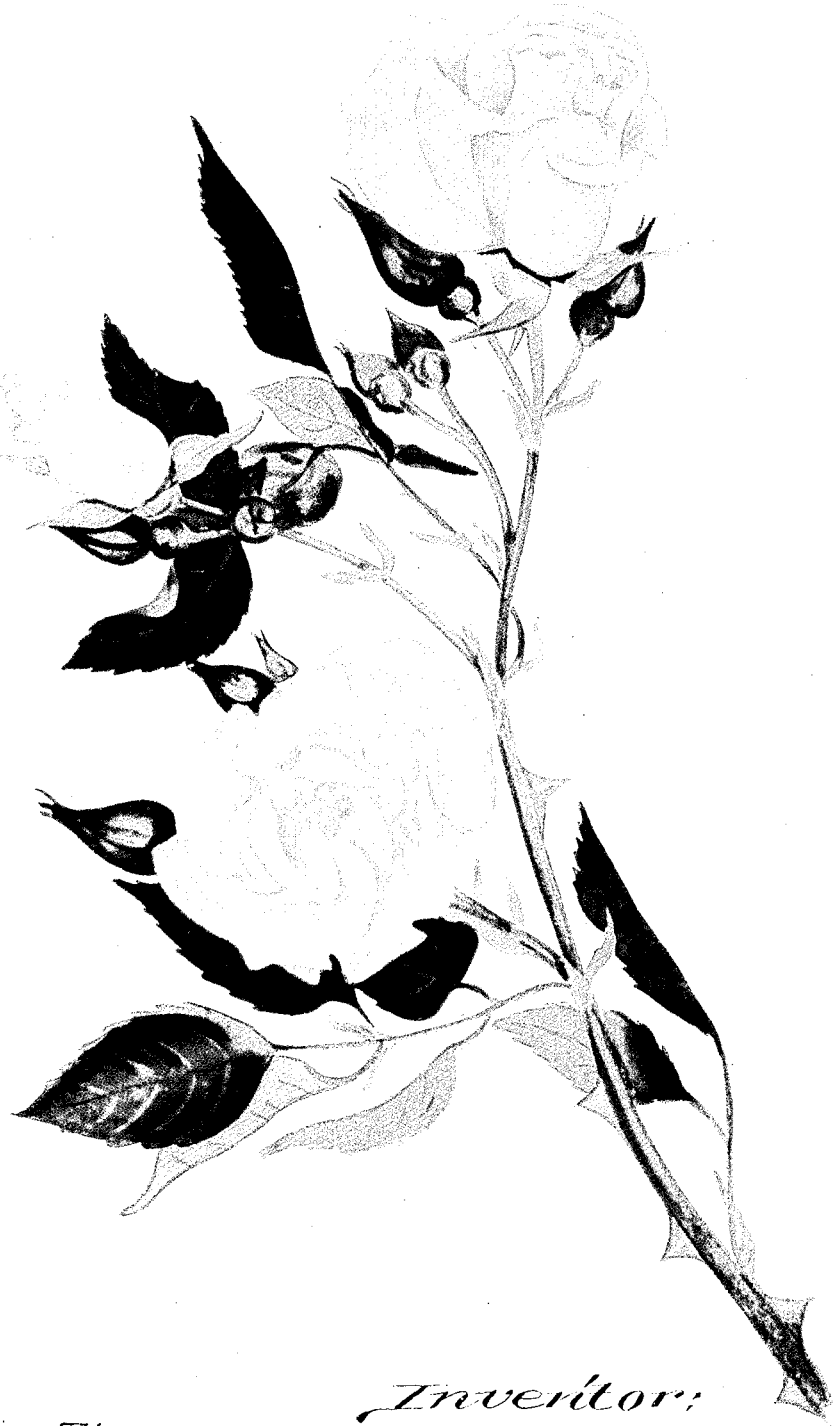
Inventor:
Elizabeth Waters Burbank, Executrix of
the Estate of Luther Burbank, Deceased
By Robb & Robb Attorneys.

Patented May 16, 1933

Plant Pat. 66

UNITED STATES PATENT OFFICE

LUTHER BURBANK, DECEASED, LATE OF SANTA ROSA, CALIFORNIA, BY ELIZABETH WATERS BURBANK, EXECUTRIX, OF SANTA ROSA, CALIFORNIA, ASSIGNOR TO STARK BRO'S NURSERIES & ORCHARDS COMPANY, OF LOUISIANA, MISSOURI

ROSE

Application filed July 18, 1932. Serial No. 623,280.

This invention relates to a new and distinct variety of climbing rose, the characterizing novelty residing primarily in the color of its flower so far as the class of climbing roses is concerned.

The objective in this origination was the production of a truly yellow climbing rose that would be hardy enough to withstand the climatic conditions prevailing in most sections of the United States where temperatures frequently go to zero or below.

The present creation, as indicated by asexual reproduction and tests, demonstrates the hardiness desired as well as permanence of the color characteristic throughout the blooming period. It is well known that most "so-called" hardy yellow climbers have a light lemon yellow bud which fades to a white rose when in full bloom, but this new rose holds its rich golden yellow color when it opens into a large blossom and until it sheds.

Generally speaking, this new climber is marked by its large yellow blossom resembling in size, color and appearance the well-known "Sunburst" variety, the petals being curled and cupped.

The buds are long and pointed with curled and ruffled edges; in color, as before mentioned, a rich golden yellow, often tipped with orange red, and are borne on long stems.

Another important feature of distinction is found in the disease resistant foliage which is a glossy "holly-like" dark green and leathery,—almost the shape of holly leaves.

In its habit of growth, it is very spreading, quite like the Dr. Van Fleet in this respect.

What is claimed is:

A new and distinct variety of hardy climbing rose, characterized by the golden yellow color of its blossom and the persistence of this color without fading until the petals fall.

In testimony whereof I affix my signature.

ELIZABETH WATERS BURBANK,
*Executrix of the Estate of Luther Burbank, Deceased.*